US012565643B2

(12) United States Patent
Medin et al.

(10) Patent No.: US 12,565,643 B2
(45) Date of Patent: Mar. 3, 2026

(54) ALPHA-GALACTOSIDASE PROTEIN FOR ENZYME REPLACEMENT THERAPY (ERT) AND METHODS OF USE

(71) Applicant: The Medical College of Wisconsin, Inc., Milwaukee, WI (US)

(72) Inventors: Jeffrey A. Medin, Shorewood, WI (US); Simone Scalia, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 655 days.

(21) Appl. No.: 17/640,246

(22) PCT Filed: Sep. 18, 2020

(86) PCT No.: PCT/US2020/051570
§ 371 (c)(1),
(2) Date: Mar. 3, 2022

(87) PCT Pub. No.: WO2021/055801
PCT Pub. Date: Mar. 25, 2021

(65) Prior Publication Data
US 2022/0348896 A1     Nov. 3, 2022

Related U.S. Application Data

(60) Provisional application No. 62/902,211, filed on Sep. 18, 2019.

(51) Int. Cl.
| | |
|---|---|
| *C12N 9/40* | (2006.01) |
| *A61K 38/00* | (2006.01) |
| *A61K 48/00* | (2006.01) |

(52) U.S. Cl.
CPC .... *C12N 9/2465* (2013.01); *C12Y 302/01022* (2013.01); *A61K 38/00* (2013.01); *A61K 48/00* (2013.01)

(58) Field of Classification Search
CPC .............................................. C12Y 302/01022
See application file for complete search history.

(56) References Cited

U.S. PATENT DOCUMENTS

| | | | |
|---|---|---|---|
| 6,013,516 | A | 1/2000 | Verma et al. |
| 6,207,455 | B1 | 3/2001 | Chang |
| 6,235,522 | B1 | 5/2001 | Kingsman et al. |
| 6,277,633 | B1 | 8/2001 | Olsen |
| 6,326,007 | B1 | 12/2001 | Yilma et al. |
| 6,627,442 | B1 | 9/2003 | Humeau et al. |
| 7,045,508 | B2 | 5/2006 | Scaria |
| 7,575,924 | B2 | 8/2009 | Trono et al. |
| 7,968,332 | B2 | 6/2011 | Charneau et al. |
| 8,329,462 | B2 | 12/2012 | Trono et al. |
| 8,349,606 | B2 | 1/2013 | Charneau et al. |
| 8,551,773 | B2 | 10/2013 | Trono et al. |
| 8,652,807 | B2 | 2/2014 | Charneau et al. |

| | | | | |
|---|---|---|---|---|
| 9,023,646 | B2 | 5/2015 | Trono et al. | |
| 9,387,236 | B2 | 7/2016 | Olmstead | |
| 9,476,062 | B2 | 10/2016 | Trono et al. | |
| 9,662,375 | B2 | 5/2017 | Jensen et al. | |
| 9,988,644 | B2 | 6/2018 | Heffner et al. | |
| 10,501,759 | B2 | 12/2019 | Heffner et al. | |
| 10,532,085 | B2 | 1/2020 | Jensen et al. | |
| 10,584,351 | B2 | 3/2020 | Roeth et al. | |
| 10,907,177 | B2 | 2/2021 | Heffner et al. | |
| 11,118,192 | B2* | 9/2021 | Kirn .......................... | C12N 7/00 |
| 11,149,285 | B2 | 10/2021 | Bosch Tubert et al. | |
| 11,571,407 | B2 | 2/2023 | Farrera-Sinfreu et al. | |
| 11,834,668 | B2 | 12/2023 | Heffner et al. | |
| 2002/0123471 | A1 | 9/2002 | Uberla | |
| 2012/0315263 | A1 | 12/2012 | Olmstead | |
| 2013/0195800 | A1 | 8/2013 | Roeth et al. | |
| 2013/0230506 | A1 | 9/2013 | Jensen et al. | |
| 2014/0010861 | A1 | 1/2014 | Bancel et al. | |
| 2014/0234278 | A1 | 8/2014 | Heffner et al. | |
| 2016/0208285 | A1 | 7/2016 | Roeth et al. | |
| 2016/0296563 | A1 | 10/2016 | Sourdive et al. | |
| 2016/0317489 | A1 | 11/2016 | Farrera-Sinfreu et al. | |
| 2016/0317627 | A1 | 11/2016 | Olmstead | |
| 2017/0056558 | A1 | 3/2017 | Kajaste-Rudnitski et al. | |
| 2017/0088859 | A1 | 3/2017 | Bosch Tubert et al. | |
| 2017/0165303 | A1 | 6/2017 | Olmstead | |
| 2017/0266263 | A1 | 9/2017 | Jensen et al. | |
| 2017/0360900 | A1 | 12/2017 | Agard et al. | |
| 2018/0002719 | A1 | 1/2018 | Roeth et al. | |
| 2018/0185415 | A1* | 7/2018 | Kohn .......................... | A61P 7/04 |

(Continued)

FOREIGN PATENT DOCUMENTS

| | | | |
|---|---|---|---|
| EP | 3293259 | A1 | 3/2018 |
| WO | 9904026 | A2 | 1/1991 |

(Continued)

OTHER PUBLICATIONS

Kukacka et al. ChemMedChem 2018, 13, 909-915 (Year: 2018).*
Schvarcz and Steward, Virology 518 (2018) 423-433 (Year: 2018).*
Friedberg, Brief. Bioinformatics (2006) 7: 225-242 (Year: 2006).*
Thorton et al. Nature structural biology, structural genomics supplement, Nov. 2000, pp. 991-994 (Year: 2000).*
Agrahari, V. et al., How Are We Improving the Delivery to Back of the Eye? Advances and Challenges of Novel Therapeutic Approaches, Expert Opinion on Drug Delivery, 2017, 14(10):1145-1162.
Biffi, A. et al., Lentiviral Hematopoietic Stem Cell Gene Therapy Benefits Metachromatic Leukodystrophy, Science, 2013, 341(6148):1-16.

(Continued)

*Primary Examiner* — Melenie L Gordon
*Assistant Examiner* — Jessica Faye Edwards
(74) *Attorney, Agent, or Firm* — Quarles & Brady LLP

(57) ABSTRACT

The present disclosure provides less immunogenic mutant α-galactosidase A protein (α-gal), methods of making and methods of use. The less immunogenic mutant α-gal of the present invention provides a reduced immune response when administered to a subject.

5 Claims, 14 Drawing Sheets
Specification includes a Sequence Listing.

(56)                    References Cited

U.S. PATENT DOCUMENTS

| | | | |
|---|---|---|---|
| 2018/0363004 A1 | 12/2018 | Heffner et al. |
| 2020/0048657 A1 | 2/2020 | Heffner et al. |
| 2020/0121740 A1 | 4/2020 | Olmstead |
| 2020/0181582 A1 | 6/2020 | Medin et al. |
| 2020/0188492 A1 | 6/2020 | Jensen et al. |
| 2020/0239906 A1 | 7/2020 | Roeth et al. |
| 2021/0171980 A1 | 6/2021 | Heffner et al. |
| 2022/0374361 A1 | 11/2022 | Jensen et al. |

FOREIGN PATENT DOCUMENTS

| | | | | | |
|---|---|---|---|---|---|
| WO | 0134843 A1 | 5/2001 | | |
| WO | 03029412 A2 | 4/2003 | | |
| WO | 03029414 A2 | 4/2003 | | |
| WO | 2009114942 A1 | 9/2009 | | |
| WO | 2016183593 A2 | 11/2016 | | |
| WO | 2017093464 A1 | 6/2017 | | |
| WO | 2018132667 A1 | 7/2018 | | |
| WO | 2019046815 A1 | 3/2019 | | |
| WO | WO-2021026447 A1 * | 2/2021 | ........... | A61K 31/445 |

OTHER PUBLICATIONS

Brady, R. et al., Enzymatic Defect in Fabry's Disease: Ceramidetrihexosidase Deficiency, New England Journal of Medicine, 1967, 276(21):1163-1167.

Brady, R. et al., Replacement Therapy for Inherited Enzyme Deficiency: Use of Purified Ceramidetrihexosidase in Fabry's Disease, New England Journal of Medicine, 1973, 289:9-14.

Cooper, D. et al., Immunobiological Barriers to Xenotransplantation, International Journal of Surgery, 2015, 23:211-216.

Dahl, M. et al., Lentiviral Gene Therapy Using Cellular Promoters Cures Type 1 Gaucher Disease in Mice, Molecular Therapy, 2015, 23(5):835-844.

Domm, J. et al., Gene Therapy for Fabry Disease: Progress, Challenges, and Outlooks on Gene-Editing, Molecular Genetics and Metabolism, 2021, 134:117-131.

Dunbar, C. et al.,Retroviral Transfer of the Glucocerebrosidase Gene into CD34+ Cells from Patients with Gaucher Disease: In Vivo Detection of Transduced Cells Without Myeloablation, Human Gene Therapy, 1998, 9(17):2629-2640.

Fowler, D. et al., Phase 2 Clinical Trial of Rapamycin-Resistant Donor CD4+ Th2/Th1 (T-Rapa) Cells After Low-Intensity Allogeneic Hematopoietic Cell Transplantation, Blood, 2013, 121(15):2864-2874.

Gargulak, K. et al., Post-Infusion Cell Enrichment: Gaucher Disease as a Model, Molecular Therapy, 2018, 26(5S1):253-254.

Harrison, F. et al., Hematopoietic Stem Cell Gene Therapy for the Multisystemic Lysosomal Storage Disorder Cystinosis, Molecular Therapy, 2013, 21(2):433-444.

Huang, J. et al., Lentivector Iterations and Pre-Clinical Scale-Up/Toxicity Testing: Targeting Mobilized CD34+ Cells for Correction of Fabry Disease, Molecular Therapy Methods & Clinical Development, 2017, 5:241-258.

Ikehara, S. et al., Grand Challenges in Stem Cell Treatments, Frontiers in Cell and Developmental Biology, 2013, vol. 1, Article 2, pp. 1-2.

Ikonomou, L. et al., Unproven Stem Cell Treatments for Lung Disease—An Emerging Public Health Problem, American Journal of Respiratory and Critical Care Medicine, 2017, 195:P13-P14.

Jonnalagadda, M. et al., Engineering Human T Cells for Resistance to Methotrexate and Mycophenolate Mofetil as an In Vivo Cell Selection Strategy, PloS One, 2013, 8(6):e65519, pp. 1-10.

Kim, E. et al., Long-Term Expression of the Human Glucocerebrosidase Gene In Vivo After Transplantation of Bone-Marrow-Derived Cells Transformed with a Lentivirus Vector, Journal of Gene Medicine, 2005, 7:878-887.

Liu, X. et al., The Immunogenicity and Immune Tolerance of Pluripotent Stem Cell Derivatives, Frontiers in Immunology, 2017, vol. 8, Article 645, pp. 1-6.

Medin, J. et al., Correction in Trans for Fabry Disease: Expression, Secretion and Uptake of Alpha-Galactosidase A in Patient-Derived Cells Driven by a High-Titer Recombinant Retroviral Vector, Proceedings of the National Academy of Sciences, 1996, 93:7917-7922.

Miller, J. et al., Glycolipid Storage and Phenotypes in a New Rat Model of Fabry Disease, The FASEB Journal, 2017, 31(S1):953.2.

Nagree, M. et al., Towards In Vivo Amplification: Overcoming Hurdles in the Use of Hematopoietic Stem Cells in Transplantation and Gene Therapy, World Journal of Stem Cells, 2015, 7(11):1233-1250.

Nagree, M. et al., In Vivo Enrichment of Transduced Cells to Enhance Gene Therapy for Fabry Disease, Molecular Genetics and Metabolism, 2018, 123:S102-S103.

Nagree, M. et al., An In Vivo Enrichment Platform to Enhance Hematopoietic Cell-Directed Gene Therapy, Molecular Therapy, 2018, 26(5S1):253.

Nagree, M. et al., An Update on Gene Therapy for Lysosomal Storage Disorders, Expert Opinion on Biological Therapy, 2019, 19(7):655-670.

Naldini, L. et al., In Vivo Gene Delivery and Stable Transduction of Nondividing Cells by a Lentiviral Vector, Science, 1996, 272(5259):263-267.

National Institute of Neurological Disorders and Stroke, What is Fabry Disease?, https://www.ninds.nih.gov/health-information/disorders/fabry-disease, 2023, 2 pages.

Pacienza, N. et al., Lentivector Transduction Improves Outcomes Over Transplantation of Human HSCs Alone in NOD/SCID/Fabry Mice, Molecular Therapy, 2012, 20(7):1454-1461.

Rombach, S. et al., Long Term Enzyme Replacement Therapy for Fabry Disease: Effectiveness on Kidney, Heart and Brain, Orphanet Journal of Rare Diseases, 2013, 8:47, pp. 1-9.

Sands, M. et al., Gene Therapy for Lysosomal Storage Diseases, Molecular Therapy, 2006, 13(5):839-849.

Sangiolo, D. et al., Lentiviral Vector Conferring Resistance to Mycophenolate Mofetil and Sensitivity to Ganciclovir for In Vivo T-cell Selection, Gene Therapy, 2007, 14:1549-1554.

Shi, Q. et al., Lentivirus-Mediated Platelet-Derived Factor VIII Gene Therapy in Murine Haemophilia A, Journal of Thrombosis and Haemostasis, 2007, 5:352-361.

Singh, R. et al., Protein Engineering Approaches in the Post-Genomic Era, Current Protein and Peptide Science, 2017, 18:1-11.

Wang, J. et al., Engineering Lentiviral Vectors for Modulation of Dendritic Cell Apoptotic Pathways, Virology Journal, 2013, 10:240, pp. 1-12.

Wu, K. et al., Cell Delivery in Cardiac Regenerative Therapy, Ageing Research Reviews, 2012, 11:32-40.

Yam, P. et al., Ex Vivo Selection and Expansion of Cells Based on Expression of a Mutated Inosine Monophosphate Dehydrogenase 2 after HIV Vector Transduction: Effects on Lymphocytes, Monocytes, and CD34+ Stem Cells, Molecular Therapy, 2006, 14(2):236-244.

Yoshimitsu, M., et al., Bioluminescent Imaging of a Marking Transgene and Correction of Fabry Mice by Neonatal Injection of Recombinant Lentiviral Vectors, Proceedings of the National Academy of Sciences, 2004, 101(48):16909-16914.

Yu, X. et al., Lentiviral Vectors with Two Independent Internal Promoters Transfer High-Level Expression of Multiple Transgenes to Human Hematopoietic Stem-Progenitor Cells, Molecular Therapy, 2003, 7(6):827-838.

Zhang, M. et al., Propagated Perturbations from a Peripheral Mutation Show Interactions Supporting WW Domain Thermostability, Structure, 2018, 26:1474-1485.

Zufferey, R. et al., Multiply Attenuated Lentiviral Vector Achieves Efficient Gene Delivery In Vivo, Nature Biotechnology, 1997, 15(9):871-875.

PCT International Search Report and Written Opinion, PCT/US2020/051570, Feb. 10, 2021, 12 pages.

* cited by examiner

FIG. 6

| Epitope 58-72 | Epitope 74-101 | 254-262 | 309-323 | 338-352 |
|---|---|---|---|---|
| E66P | D83E | | P323R | |
| E58N | A84I | | | |
| M70A | | | | |
| M70R | S78D | | A309N | |
| M70N | | | | |
| D61N | M70D | | | |
| M70G | S78E | A84V | | |
| M70H | | Y86L | | |
| M70Q | | | | |
| M70I | | | | |
| M70L | | | | |
| M70K | S78V | | | |
| S62R | E79A | R100F | | |
| M70P | E79N | D101N | | |
| S62N | E79D | D101E | | |
| E59N | E79G | | A318G | |
| S62T | | | | |

Lysate

M   S62N   M70G   E79D   E79G   R100F   D101E   NC   WT

75 KDa

50 KDa

37 KDa

ALPHA-GALACTOSIDASE PROTEIN FOR ENZYME REPLACEMENT THERAPY (ERT) AND METHODS OF USE

CROSS-REFERENCE TO RELATED APPLICATIONS

This patent application represents the national stage entry of PCT/US2020/051570, filed Sep. 18, 2020 and claims the benefit of priority of U.S. Provisional Patent Application No. 62/902,211, filed Sep. 18, 2019, which is incorporated herein by reference in its entirety.

STATEMENT REGARDING FEDERALLY SPONSORED RESEARCH

N/A

SEQUENCE LISTING

A Sequence Listing accompanies this application and is submitted as an ASCII text file of the sequence listing named "650053_00731_ST25.txt" which is 6.87 KB in size and was created on Sep. 15, 2020. The sequence listing is electronically submitted via EFS-Web with the application and is incorporated herein by reference in its entirety.

BACKGROUND OF THE INVENTION

The field of the invention is mutated alpha galactosidase with reduced immunogenicity for use in the treatment of Fabry disease.

Fabry disease (FD) is a lysosomal storage disease (LSD) resulting from a deficiency in the enzyme $\alpha$-galactosidase A ($\alpha$-gal A encoded by the AGA transgene), an enzyme that hydrolyses $\alpha$-galactose from glycosphingolipids, in particular globotriaosylceramide ($Gb_3$). Lysosomal Storage Disorders (LSD) are a group of more than 70 rare inherited metabolic disorders that result from lysosome dysfunction, usually as a consequence of a deficiency in a single enzyme required for the intracellular digestion of lipids, glycoproteins or polysaccharides. Because of such deficiencies, the molecules that would normally be degraded accumulate inside the cell, leading to dysfunction or death of the cell.

The standard-of-care treatment for Fabry disease is enzyme replacement therapy (ERT. aka ET). The efficacy of ERT is outlined by Rombach et al. (Orphanet J Rare Dis. 8:47-10.1186/1750-1172-8-47 (2013)). While some benefits can be obtained, disease progression is not halted. ERT requires lengthy intravenous infusions of $\alpha$-gal administered every couple of weeks, often at an outpatient center. Although Fabry disease is relatively rare, there are about 4000 patients in the US, treatment costs are on the order of $300,000/year/patient ($1.2 B/year for all US patients).

Fabry patients sometimes have an immune reaction to the ERT. Therefore, there is a need for less immune reactive $\alpha$-gal A that can be used for enzyme replacement therapy.

SUMMARY OF THE INVENTION

The present invention overcomes the aforementioned drawbacks by providing mutant $\alpha$-galactosidase A proteins that are less immunogenic, nucleotides encoding the mutant $\alpha$-galactosidase A proteins, and methods of making and using the same.

In one aspect, the present invention provides less immunogenic mutant $\alpha$-galactosidase A protein ($\alpha$-gal) comprising one or more amino acid changes in one or more antigenic epitopes, wherein the one or more antigenic epitopes are selected from the group consisting of (a) LHWERF (SEQ ID NO:2; position 45-50 of $\alpha$-gal), (b) DCQEEPDSCI (SEQ ID NO:3; position 55-64 of $\alpha$-gal), (c) FMEMAELMVSEQ (SEQ ID NO:4; position 69-79 of $\alpha$-gal), (d) KDAGYEY (SEQ ID NO:5; position 82-88 of $\alpha$-gal), (e) DDCWMA (SEQ ID NO:6; position 92-97 of $\alpha$-gal),(f) EGRLQADPQRF (SEQ ID NO:7; position 103-113 of $\alpha$-gal), (g) TCAGF (SEQ ID NO:8; position 141-145 of $\alpha$-gal), (h) DIDAQTF (SEQ ID NO:9; position 153-159 of $\alpha$-gal), (i) DLLKFDGC (SEQ ID NO:10; position 165-172 of $\alpha$-gal), (j) ENLAD (SEQ ID NO:11; position 178-182 of $\alpha$-gal), (k) IVYSCEW (SEQ ID NO:12; position 198-204 of $\alpha$-gal), (l) PLYMWPFQ (SEQ ID NO:13; position 205-212 of $\alpha$-gal), (m) YCNHW (SEQ ID NO:14; position 222-226 of $\alpha$-gal), (n) SWKSI (SEQ ID NO:15; position 235-239 of $\alpha$-gal), (o) LDWTSFNQER (SEQ ID NO:16; position 243-252 of $\alpha$-gal), (p) IVDVA (SEQ ID NO:17; position 253-257 of $\alpha$-gal), (q) NDPDML (SEQ ID NO:18; position 263-268 of $\alpha$-gal), (r) ALLQD (SEQ ID NO:19; position 309-313 of $\alpha$-gal), (s) QLRQGDNF (SEQ ID NO:20; position 330-337 of $\alpha$-gal), (t) EVWERPLSG (SEQ ID NO:21; position 338-346 of $\alpha$-gal), (u) WAVAMIN (SEQ ID NO:22; position 349-355 of $\alpha$-gal), and (v) EIGGPRSY (SEQ ID NO:23; position 358-365 of $\alpha$-gal), wherein the mutant $\alpha$-gal retains enzymatic function and is less immunogenic than the non-mutated $\alpha$-gal.

In another aspect, an expression construct comprising a nucleic acid sequence encoding the mutant $\alpha$-gal described herein is contemplated.

In another aspect, the disclosure provides a cell able to express the mutant $\alpha$-gal described herein. In one example, the cell is a patient's cell. In another example, the patient cell is used for therapy.

In another aspect, the disclosure provides a method of producing a mutant $\alpha$-gal, the method comprising: a) expressing the mutant $\alpha$-gal in a cell; and (b) isolating and purifying the mutant $\alpha$-gal protein from the cell, wherein the mutant $\alpha$-gal has enzymatic activity.

In another aspect, the disclosure provides a method of treating Fabry disease in a subject, the method comprising the steps of: (a) administering a therapeutically effective amount of the disclosed mutant $\alpha$-gal protein to treat Fabry disease and reduce one or more symptoms of the lysosomal storage disorder.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

FIG. 6. Novel α-gal A variants were selected using software to identify mutations that are predicted to maintain enzyme functionality (software used: PolyPhen-2) while reducing immunogenicity (databases used: CTLpred, Immunomedicine group, MHCBP, IEDB.org, SVRMHC, BcePred, SVMTrip, PREDIVAC, EpiJen). Notably, these mutations are found in three of the five reactive epitopes identified in Example 1. In many cases there are multiple amino acid changes possible per mutation predicted to retain functionality while reducing immunogenicity. Red boxes are used to highlight the six mutations that were selected for in vitro analysis in Example 3.

DETAILED DESCRIPTION OF THE INVENTION

Figure 1A:
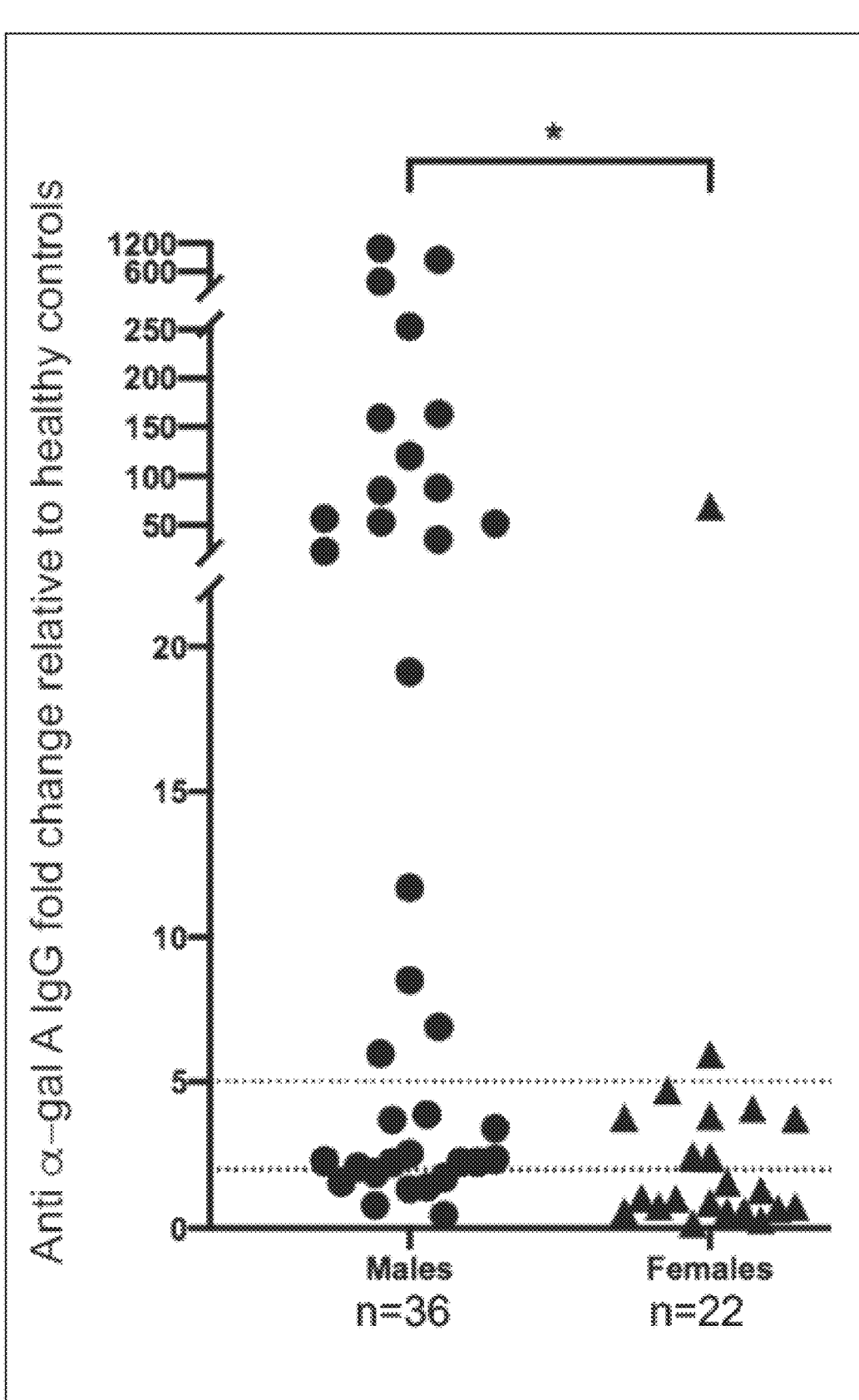
FIG. 1A. Sera from 58 male and female FD patients were analyzed for the presence of anti-$\alpha$-gal A IgG by ELISA. High levels (>5-fold greater than healthy donors) of antibody against $\alpha$-gal A were found in 21 patients (36%). Male patients showed a statistically significant higher level of anti-$\alpha$-gal A IgG in comparison to females. Dashed line at 2 indicates cut-off for low-titer patients. *$p < 0.05$, Mann-Whitney U test.

The present disclosure provides improved mutant alpha galactosidase A protein (α-gal A) for use in treating Fabry disease (FD). Particularly, the present invention describes a mutant α-gal A protein that has reduced immunogenicity in a subject while maintaining its enzymatic function, and methods of using the mutant α-gal to deliver therapeutic products to a subject in need thereof.

FD is an α-gal A deficiency in which globotriaosylceramide (Gb$_3$) and other metabolites accumulate. Standard of care for Fabry patients has been enzyme replacement therapy (ERT), e.g., regular treatment with exogenous α-galactosidase A. For example, in the United States there is a commercially approved Enzyme Replacement Therapy (ERT) to treat Fabry disease called agalsidase beta (agalsidase-β, Fabrazyme®) produced by Sanofi-Genzyme (produced in Chinese hamster ovary cells). It is administered by intravenous infusion usually every two weeks. The approved dose is 1 milligrams per kilogram of body weight. In Europe and many other countries but not in the United States, there is also a commercially approved intravenous Enzyme Replacement Therapy (ERT) to treat Fabry disease called agalsidase alfa (agalsidase-α, Replagal®) produced by Shire (produced from a modified human fibrosarcoma cell line). It is also administered by intravenous infusion usually every two weeks. The approved dose is 0.2 milligrams per kilogram of body weight. Two new plant-based products are currently in development: pegunigalsidase α, (Protalix Biotherapeutics), which is produced in BY2 tobacco cells, and moss-αGal (Greenovation), which is produced in moss.

The immune responses, including humoral immune responses following enzyme replacement therapy have been described in the literature for Fabry disease.

The mutations discovered in the present invention described herein may be useful in the reduction of the immune response for the ERTs already on the market. By incorporating one or more of the mutations described herein in turn reduces the immune response toward the exogenous α-gal and one or more of the associated side effects. The ability to reduce the immune response to the exogenously derived α-gal in turn increases the efficacy of the ERT. Not to be bound by theory, the ability to reduce the immunogenicity of the exogenous α-gal A protein reduces the humoral responses to exogenous protein, in effect decreasing the likelihood of producing neutralizing antibodies to the exogenous α-gal protein, and thus increasing the efficacy of ERT by avoiding reduced efficacy caused by neutralizing antibodies to the exogenous protein.

The mutant α-gal A proteins of the present disclosure are provided that reduce the immune reaction to exogenously administered α-gal in a patient with Fabry disease. By "reduced immune reaction" the present mutant α-gal elicit a reduced immune reaction to the exogenously administered α-gal protein in a subject having Fabry disease. The immune reaction includes a humoral (antibody) response to the α-gal protein, which may include neutralizing antidrug antibodies (ADAs) which can attenuate the therapeutic efficacy of ERT in a subset of patients.

For clarity, epitopes of α-gal are described herein using position numbers based on the α-gal protein sequence of SEQ ID NO:1 (NCBI ref: NP_000160.1). However, the amino acid changes of α-gal mutant described herein can be incorporated into other α-gal known in the art that can be used for ERT, including other altered α-gal proteins which may already have some changes within the protein sequence. One skilled in the art would be able to align the protein sequences and translate the position numbers of the epitopes described herein into other known α-gal proteins. Thus, it is contemplated that changes in one or more epitopes that reduce the immunogenicity can be applied to other protein sequences of α-gal known in the art and are part of the present invention. As discussed more below, the ability to test the immunogenicity is well within one skilled in the art taking into account the teachings of the present invention.

In one embodiment, the present disclosure provides a less immunogenic mutant α-galactosidase A protein (α-gal) comprising one or more amino acid changes in one or more antigenic epitopes, wherein the one or more antigenic epitopes are selected from the group consisting of (a) LHWERF (SEQ ID NO:2; position 45-50 of α-gal), (b) DCQEEPDSCI (SEQ ID NO:3; position 55-64 of α-gal), (c) FMEMAELMVSEQ (SEQ ID NO:4; position 69-79 of α-gal), (d) KDAGYEY (SEQ ID NO:5; position 82-88 of α-gal), (e) DDCWMA (SEQ ID NO:6; position 92-97 of α-gal), (f) EGRLQADPQRF (SEQ ID NO:7; position 103-113 of α-gal), (g) TCAGF (SEQ ID NO:8; position 141-145 of α-gal), (h) DIDAQTF (SEQ ID NO:9; position 153-159 of α-gal), (i) DLLKFDGC (SEQ ID NO:10; position 165-172 of α-gal), (j) ENLAD (SEQ ID NO:11; position 178-182 of α-gal), (k) IVYSCEW (SEQ ID NO:12; position 198-204 of α-gal), (l) PLYMWPFQ (SEQ ID NO:13; position 205-212 of α-gal), (m) YCNHW (SEQ ID NO:14; position 222-226 of α-gal), (n) SWKSI (SEQ ID NO:15; position 235-239 of α-gal), (o) LDWTSFNQER (SEQ ID NO:16; position 243-252 of α-gal), (p) IVDVA (SEQ ID NO:17; position 253-257 of α-gal), (q) NDPDML (SEQ ID NO:18; position 263-268 of α-gal), (r) ALLQD (SEQ ID NO:19; position 309-313 of α-gal), (s) QLRQGDNF (SEQ ID NO:20; position 330-337 of α-gal), (t) EVWERPLSG (SEQ ID NO:21; position 338-346 of α-gal), (u) WAVAMIN (SEQ ID NO:22; position 349-355 of α-gal), and (v) EIGGPRSY (SEQ ID NO:23; position 358-365 of α-gal), wherein the mutant α-gal retains enzymatic function and is less immunogenic than the wild-type or non-mutated α-gal. These mutations are relative to SEQ ID NO:1. In another example, the disclosure provides a less immunogenic mutant α-gal protein comprising one or more amino acid changes in two or more antigenic epitopes selected from the group consisting of (a)-(v), alternatively three or more antigenic epitopes selected from the group consisting of (a)-(v), alternatively four or more antigenic epitopes selected from the group consisting of (a)-(v), alternatively five or more or more antigenic epitopes selected from the group consisting of (a)-(v), and alternatively comprises two or more amino acid changes within the one or more epitopes relative to SEQ ID NO:1.

In some embodiments, the less immunogenic mutant α-gal comprises one or more, alternatively two or more, alternatively three or more amino acid changes in two or more antigenic epitopes selected from the group consisting of (a)-(v), wherein the mutant α-gal retains enzymatic function and is less immunogenic than the non-mutated α-gal.

In one example, the mutant α-gal comprises changes in three or more antigenic epitopes selected from the group consisting of (a)-(v), wherein the mutant α-gal retains enzymatic function and is less immunogenic than the non-mutated α-gal.

As described in the Examples, the epitopes were identified in male and female Fabry patients that where immunogenic as listed in Table 1. Computer analysis of the epitopes was run to determine amino acid changes that allow for the retention of the enzymatic function but reduce the immunogenicity of the epitope within the α-gal.

In another example, the one or more amino acid changes are found in the one or more of the epitopes selected from the group consisting of (a) LHWERF (SEQ ID NO:2; position 45-50 of α-gal), (b) DCQEEPDSCI (SEQ ID NO:3;

position 55-64 of α-gal), (c) FMEMAELMVSEQ (SEQ ID NO:4; position 69-79 of α-gal), (d) KDAGYEY (SEQ ID NO:5; position 82-88 of α-gal), (e) DDCWMA (SEQ ID NO:6; position 92-97 of α-gal),(f) EGRLQADPQRF (SEQ ID NO:7; position 103-113 of α-gal), (g) TCAGF (SEQ ID NO:8; position 141-145 of α-gal), (h) DIDAQTF (SEQ ID NO:9; position 153-159 of α-gal), (i) DLLKFDGC (SEQ ID NO:10; position 165-172 of α-gal), (j) ENLAD (SEQ ID NO:11; position 178-182 of α-gal), (k) IVYSCEW (SEQ ID NO:12; position 198-204 of α-gal), (l) PLYMWPFQ (SEQ ID NO:13; position 205-212 of α-gal), (m) YCNHW (SEQ ID NO:14; position 222-226 of α-gal), (n) SWKSI (SEQ ID NO:15; position 235-239 of α-gal), (o) LDWTSFNQER (SEQ ID NO:16; position 243-252 of α-gal), (p) IVDVA (SEQ ID NO:17; position 253-257 of α-gal), (q) NDPDML (SEQ ID NO:18; position 263-268 of α-gal), (r) ALLQD (SEQ ID NO:19; position 309-313 of α-gal), (s) QLRQGDNF (SEQ ID NO:20; position 330-337 of α-gal), (t) EVWERPLSG (SEQ ID NO:21; position 338-346 of α-gal), (u) WAVAMIN (SEQ ID NO:22; position 349-355 of α-gal), and (v) EIGGPRSY (SEQ ID NO:23; position 358-365 of α-gal), alternatively two or more epitopes selected from (a), (b), (d), (i), (k), (o), (p), (q), (r), (s), (t), and (v); alternatively three or more epitopes selected from the group consisting of (a), (b), (d), (i), (k), (o), (p), (q), (r), (s), (t), and (v); alternatively four or more epitopes selected from the group consisting of (a), (b), (d), (i), (k), (o), (p), (q), (r), (s), (t), and (v), and combinations therein.

In some embodiments one or more amino acids may be altered in the epitope identified in (a)-(v), for example, two or more amino acids may be altered in the same epitope (e.g., an epitope selected from (a)-(v)), alternatively three or more amino acids may be altered in the same epitope, alternatively four or more amino acids may be altered in the same epitope.

One skilled in the art would be able to determine and test if an amino acid change that does not alter the enzymatic function, but reduces immunogenicity of the exogenous α-gal protein when administered to a subject.

Suitable mutations within the epitopes identified include an amino acid change at one or more positions within the α-gal protein, wherein the one or more positions is selected from the group consisting of 58, 59, 61, 62, 66, 70, 78, 79, 83, 84, 86, 100, 101, 309, 318, and 323 (relative to SEQ ID NO:1), wherein the amino acid change at one or more of these positions retains enzymatic function and reduces the immune reaction to exogenous α-gal in a subject.

In another example, the mutant α-gal comprises one or more amino acid change selected from the group consisting of E58N, E59N, D61N, S62R, S62N, S62T, E66P, M70A, M70R, M70N, M70D, M70G, M70H, M70Q, M70I, M70L, M70K, M70P, S78D, S78E, S78V, E79A, E79N, E79D, E79G, D83E, A84I, A84V, Y86L, R100F, D101N, D101E, A309N, A318G, and P323R, in alternative examples, the mutant α-gal comprises two or more of the amino acid changes selected from the group consisting of E58N, E59N, D61N, S62R, S62N, S62T, E66P, M70A, M70R, M70N, M70D, M70G, M70H, M70Q, M70I, M70L, M70K, M70P, S78D, S78E, S78V, E79A, E79N, E79D, E79G, D83E, A84I, A84V, Y86L, R100F, D101N, D101E, A309N, A318G, and P323R, alternatively three or more, alternatively four or more, alternatively five or more, alternatively six or more, alternatively seven or more, alternatively eight or more, alternatively nine or more, alternatively ten or more amino acid changes selected from the group consisting of E58N, E59N, D61N, S62R, S62N, S62T, E66P, M70A, M70R, M70N, M70D, M70G, M70H, M70Q, M70I, M70L, M70K, M70P, S78D, S78E, S78V, E79A, E79N, E79D, E79G, D83E, A84I, A84V, Y86L, R100F, D101N, D101E, A309N, A318G, and P323R. The mutant α-gal containing the one or more amino acid changes have maintained enzymatic function but have reduced the immunogenicity (e.g., reduced the humoral response) to the antibody.

"Percentage of sequence identity" or "sequence similarity" is determined by comparing two optimally aligned sequences over a comparison window, wherein the portion of the polypeptide or polynucleotide sequence in the comparison window may comprise substitutions, or additions or deletions (i.e., gaps) as compared to the reference sequence (which does not comprise substitutions, additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "similarity" of polypeptide or polynucleotide sequences means that a polypeptide or polynucleotide comprises a sequence that has at least 80% sequence identity. Suitable sequence similarity allows for small changes in the protein or transgene that do not affect the function of the protein expressed by the transgene. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using programs such as BLAST using standard parameters. These values can be appropriately adjusted to determine corresponding identity of proteins encoded by two nucleotide sequences by taking into account codon degeneracy, amino acid similarity, reading frame positioning and the like.

Methods of testing immunogenicity and enzymatic function are understood by one skilled in the art in view of this disclosure.

As discussed in the examples, a number of the epitopes found within the human patients were also found within mice treated with the exogenous α-gal. Therefore, one skilled in the art would be able to be use the mouse model to test and determine if reduced immunogenicity, e.g., a reduced humoral response, to the exogenous mutant α-gal. The ability to determine the enzymatic function of the protein is known in the art.

The present disclosure also provides an expression construct comprising a nucleic acid sequence encoding the mutant α-gal described herein. Expression constructs comprise a heterologous promoter and the nucleic acid sequence encoding the mutant α-gal protein which is capable of expressed and purified from a cell. The expression constructs include vectors which are capable of directing the expression of exogenous genes to which they are operatively linked. Such vectors are referred to herein as "recombinant constructs," "expression constructs," "recombinant expression vectors" (or simply, "expression vectors" or "vectors"). Suitable vectors are known in the art and contain the necessary elements in order for the gene encoded within the vector to be expressed as a protein in the host cell. The term "vector" refers to a nucleic acid molecule capable of transporting another nucleic acid to which it has been linked. One type of vector is a "plasmid", which refers to a circular double stranded DNA loop into which additional DNA segments may be ligated, specifically exogenous DNA segments encoding the mutant α-gal protein. Another type of vector is a viral vector, wherein additional DNA segments may be ligated into the viral genome. Certain vectors are capable of autonomous replication in a host cell into which they are introduced. Other vectors can be integrated into the genome of a host cell upon introduction into the host cell, and thereby are replicated along with the host genome (e.g. lentiviral vectors). Moreover, certain vectors are capable of directing the expression of exogenous genes to which they are operatively linked. In general, vectors of utility in recombinant DNA techniques are often in the form of plasmids. In the present specification "vector" include expression vectors, such as viral vectors (e.g., replication defective retroviruses (including lentiviruses), adenoviruses and adeno-associated viruses), which serve equivalent functions.

The vectors are heterogeneous exogenous constructs containing sequences from two or more different sources. Suitable vectors include, but are not limited to, plasmids, expression vectors, lentiviruses (lentiviral vectors), adeno-associated viral vectors (rAAV) among others and includes constructs that are able to express the mutant α-gal. A preferred vector is a lentiviral vector. Suitable methods of making lentiviral vector particles are known in the art to be able to transform cells in order to express the mutant α-gal described herein.

The vectors are not limited and include any vectors including lentiviral vectors capable of expressing the mutant α-gal are contemplated for use in the practice of the current invention. A vector can preferably transduce, transform or infect a cell, thereby causing the cell to express the mutant α-gal proteins encoded by the vector.

In another example, the present disclosure provides a virus comprising the expression construct capable of expressing the mutant α-gal.

In another example, a host cell able to express the mutant α-gal described herein are provided. Suitable host cells that can express the mutant α-gal protein includes any tissue culture cell, plant cell or other cell that is able to express the mutant α-gal to retain enzymatic activity. For example, suitable cell types are known in the art and include, but are not limited to, Chinese hamster ovary (CHO) cells, 293 cells, moss cells, BY2 tobacco cells, skin fibroblasts, stem cells, induced pluripotent stem cells (iPSCs), hematologic cells, T cells, liver cells, among others known in the art. Plant cells are also contemplated.

Further, the mutant α-gal proteins can also be used in methods and systems for gene therapy that are being used for treating Fabry disease. For example, mutant α-gal proteins can be used for gene therapy by incorporating the mutant α-gal into a patient's own or donor cell, particularly stem cells, for example hematopoietic stem cells (CD34+ stem cells), or other cells including T-cells, T-rapa cells, among others. For example, patient CD34+ stem cells can be transduced with the mutant α-gal and reintroduced into the patient. Suitable methods of using the mutant α-gal protein include incorporating into a viral gene therapy system (e.g., retroviral including lentiviral vector gene therapy system, AAV gene therapy system, etc.), for example, using the methods described in U.S. Patent Application Nos. PCT/US2018/036292, PCT/US2019/029639, the contents of which are incorporated by reference in their entireties.

The present disclosure also provides compositions comprising the mutant α-gal protein described herein and a pharmaceutically acceptable carrier. A "pharmaceutically acceptable carrier" means any conventional pharmaceutically acceptable carrier, vehicle, or excipient that is used in the art for production and administration of compositions to a subject. Pharmaceutically acceptable carriers are typically non-toxic, inert, solid or liquid carriers which are physiologically balanced. The pharmaceutically acceptable carriers are carriers that allow for the retention of the activity of the enzyme within the composition and they can be stably stored before administration and are known in the art. The carriers keep the proper folding of the mutant α-gal protein that allows enzymatic function. Typically, phosphate buffered saline or other saline solutions are physiologically acceptable carriers. A pharmaceutically acceptable carrier can be selected on the basis of the selected route of administration and standard pharmaceutical practice. The compounds may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa., which is incorporated by reference in its entirety. Suitable dosage forms may comprise, but are not limited to, for example, solutions, parenteral solutions, injectable solutions, troches, suppositories, or suspensions.

For parenteral administration, the active agent may be mixed with a suitable carrier or diluent such as water, an oil (e.g., a vegetable oil), ethanol, saline solution (e.g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

The pharmaceutical composition is preferably in unit dosage form. In such form the preparation is divided into unit doses containing appropriate quantities of the active component. The unit dosage form can be a packaged preparation, the package containing discrete quantities of preparation, such as packeted vials or ampoules.

In another embodiment, the present disclosure provides a method of producing a mutant α-gal, the method comprising: a) expressing the mutant α-gal described herein in a host cell; and (b) isolating and purifying the mutant α-gal protein from the host cell, wherein the mutant α-gal has enzymatic activity and lower immunogenicity compared to the wild type or non-mutant α-gal.

In another embodiment, the disclosure provides a method of treating Fabry disease in a subject, the method comprising the steps of: (a) administering a therapeutically effective amount of the mutant α-gal described herein to treat Fabry disease.

By "treating" we mean the management and care of the subject for combatting the disease, condition or disorder, particularly Fabry disease. The term treating includes the administration of a compound or composition described herein to reduce, ameliorate, or eliminate one or more symptoms of Fabry disease. For example, treating Fabry disease in a subject includes reducing or eliminating the accumulation of spingolipids/glycolipids, particularly globotriaosylceramides within the subject (e.g., reduce the accumulation within blood vessels, and other tissues and organs within the subject). Treatment thus results in the reduction in one or more symptom associated with the accumulation of the glycolipid within the subject. Symptoms vary depending on the organ affected, but include, but are not limited to, e.g., pain, kidney disease, kidney failure, abnormal thickening of the heart muscle or hypertrophy, abnormal heart rhythm, heart valve thickening, valve leakage, angiokeratomas, anhidrosis, neuropathy, fatigue, cerebrovascular effects leading to an increased risk of stroke, vertigo, verterbrobasilar system tinnitus, nausea, inability to gain weight, diarrhea, among others.

In a preferred example, the mutant α-gal is administered by intravenous transfusion.

Treating also encompasses reducing the immune response to exogenous α-gal in a subject. Reduction in the immune response in a subject includes reducing or eliminating a humoral response to exogenous α-gal (e.g., reduction in amount or number of antibodies against exogenous α-gal), reducing or eliminating neutralizing antibodies to exogenous α-gal, and/or reducing other immune response signaling. It is known that antibodies can neutralize α-gal A protein administered by ERT or gene therapy in at least a couple of ways: 1) they can bind to the circulating product in the plasma and block the normal uptake route into cells through the Mannose-6-Phosphate Receptor; 2) they can also bind to α-gal A and inhibit enzyme trafficking and activity in recipient cells. Thus the use and administrating the mutant α-gal described herein can reduce or inhibit one or more of these results of neutralizing antibodies, e.g., reduce antibody binding to the circulating product in the plasma and block the normal uptake route into cells through the Mannose-6-Phosphate Receptor; and/or reduce antibody binding to α-gal A and reduce the ability to inhibit enzyme trafficking and activity in recipient cells.

By "subject" or "patient" refers to a mammal, particularly a human, in which suffer from a disease able to be treated with exogenous α-gal. In a particular example, the subject is a human suffering from Fabry disease. Particularly, the subject is a male or female human suffering from Fabry disease.

Not to be bound by any theory, but it is advantageous to administer an α-gal A protein that has reduced immunogenicity, including the fact that reduction in the immune response that is associated with ERT will reduce the side effects and may prolong the beneficial outcomes from ERT, which will lower treatment morbidity and cost.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

Aspects of the present disclosure that are described with respect to methods can be utilized in the context of the compositions of matter or kits discussed in this disclosure. Similarly, aspects of the present disclosure that are described with respect to compositions of matter can be utilized in the context of the methods and kits, and aspects of the present disclosure that are described with respect to kits can be utilized in the context of the methods and compositions of matter.

The invention will be more fully understood upon consideration of the following non-limiting examples.

EXAMPLES

Example 1: Immunogenic Epitope Analysis of Alpha Galactosidase A

In this Example, the inventors identify immune reactive epitopes within the α-gal protein in ERT-treated FD patients. This information was used to determine amino acid substitutions that can be used to develop novel, less immunoreactive α-gal A variants for use in ERT or gene therapy, as these novel α-gal A variants may have improved clinical efficacy.

Method: Anti-α-gal A IgG titers were determined via ELISA in 6 non-treated, 28 aga α- and 22 aga β-treated FD subjects. FIG. 1A shows the results of sera from 58 male and female FD patients were analyzed for the presence of anti-α-gal A IgG by ELISA. High levels (>5-fold greater than healthy donors) of antibody against α-gal A were found in 21 patients (36%). Male patients showed a statistically significant higher level of anti-α-gal A IgG in comparison to females.

Figure 1B:
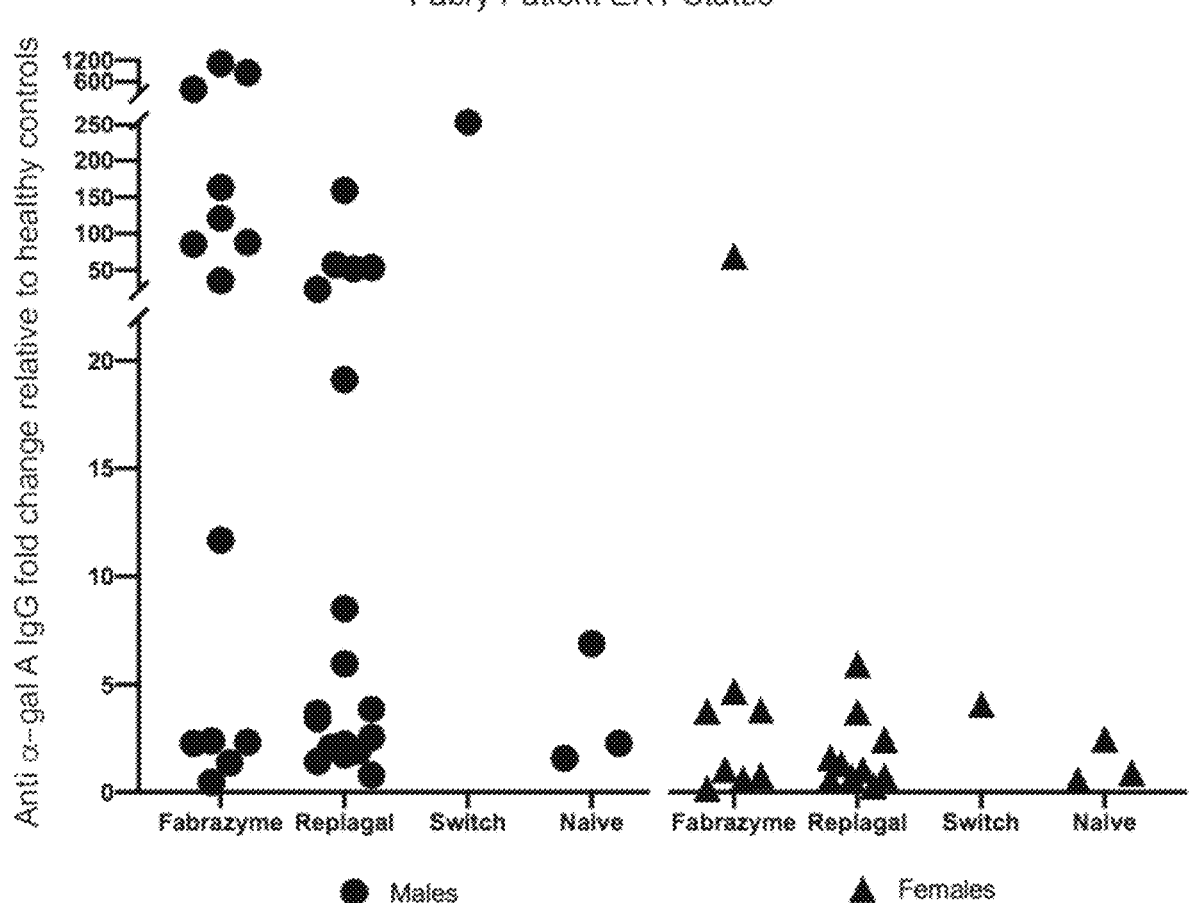
FIG. 1B. Anti α-gal A IgG levels as measured by ELISA in Fabry patients treated with Fabrazyme, Replagal, both enzyme therapies (switch), or no enzyme therapy. Male Fabry patients display higher Anti α-gal A IgG than female Fabry patients. Both Fabrazyme and Replagal treated Fabry patients both express anti-α-gal A IgG. Enzyme Therapy naïve Fabry patients also display anti-α-gal A IgG.

Also included were 2 FD patients that switched therapy from aga α to aga β. Immunogenic epitopes of α-gal A were identified by PEPperMAP technology (PEPperPRINT GmbH, Hamburg, Germany), as shown in FIG. 1B. FIG. 1B shows anti-α-gal A IgG levels as measured by ELISA in Fabry patients treated with Fabrazyme, Replagal, both enzyme therapies (switch), or no enzyme therapy. Male Fabry patients display higher anti-α-gal A IgG than female Fabry patients. Both Fabrazyme and Replagal treated Fabry patients both express anti-α-gal A IgG. Enzyme therapy naïve Fabry patients also display anti-α-gal A IgG.

Figure 2:
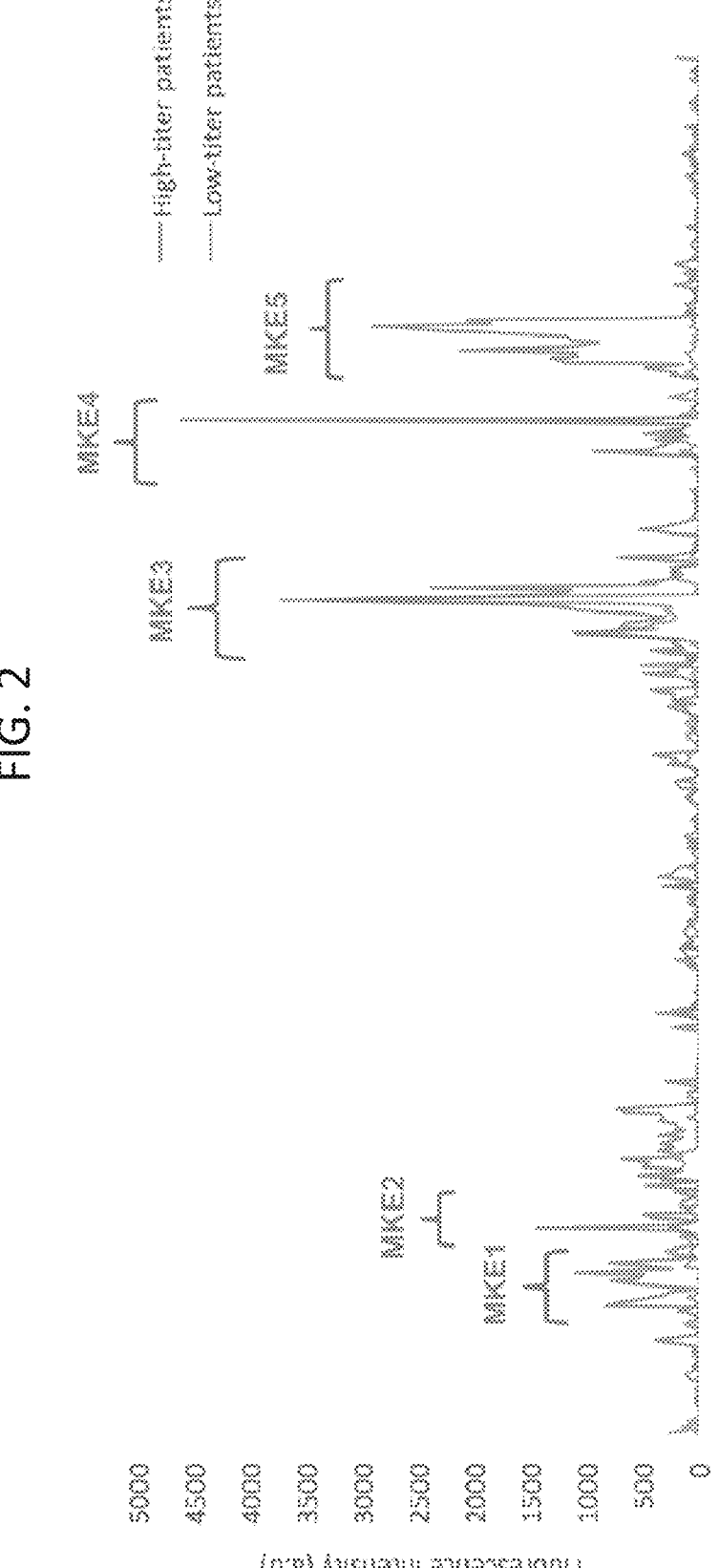
FIG. 2. Epitope mapping analysis was performed on the sera of 17 high-titer and 20 low-titer FD patients. Whereas 5 reactive epitopes of α-gal A were identified in high-titer patients, only a single epitope (MKE3) was present in low-titer patients.
Figure 3:
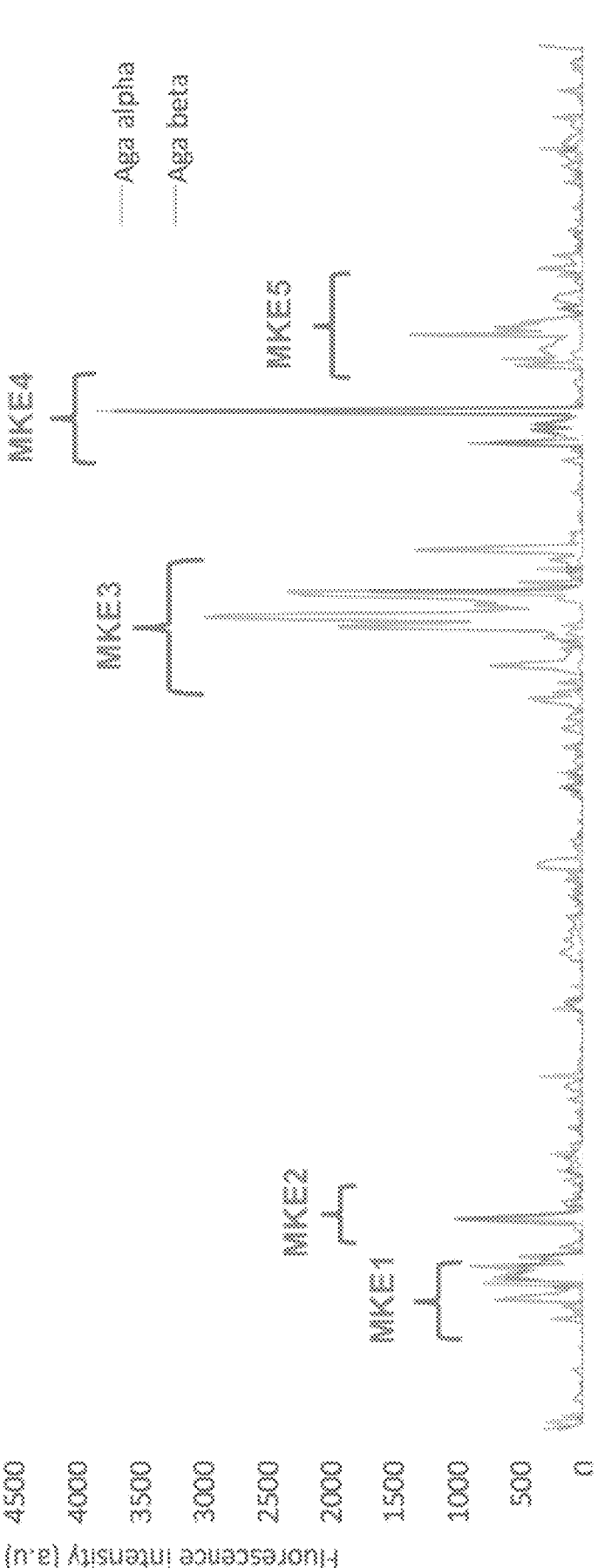
FIG. 3. Patient epitope mapping results were grouped according to their ERT therapy. Sera from aga β-treated patients contained all 5 of the previously identified epitopes while sera from aga α-treated patients was missing epitope MKE5.

FIG. 2 shows epitope mapping analysis performed on the sera of 17 high-titer and 20 low-titer FD patients. 5 reactive epitopes of α-gal A were identified in high-titer patients, while only a single epitope (MKE3) was present in low-titer patients. FIG. 3 shows patient epitope mapping results that were grouped according to their ERT therapy. Sera from aga β-treated patients contained all 5 of the previously identified epitopes while sera from aga α-treated patients was missing epitope MKES.

Figure 4:
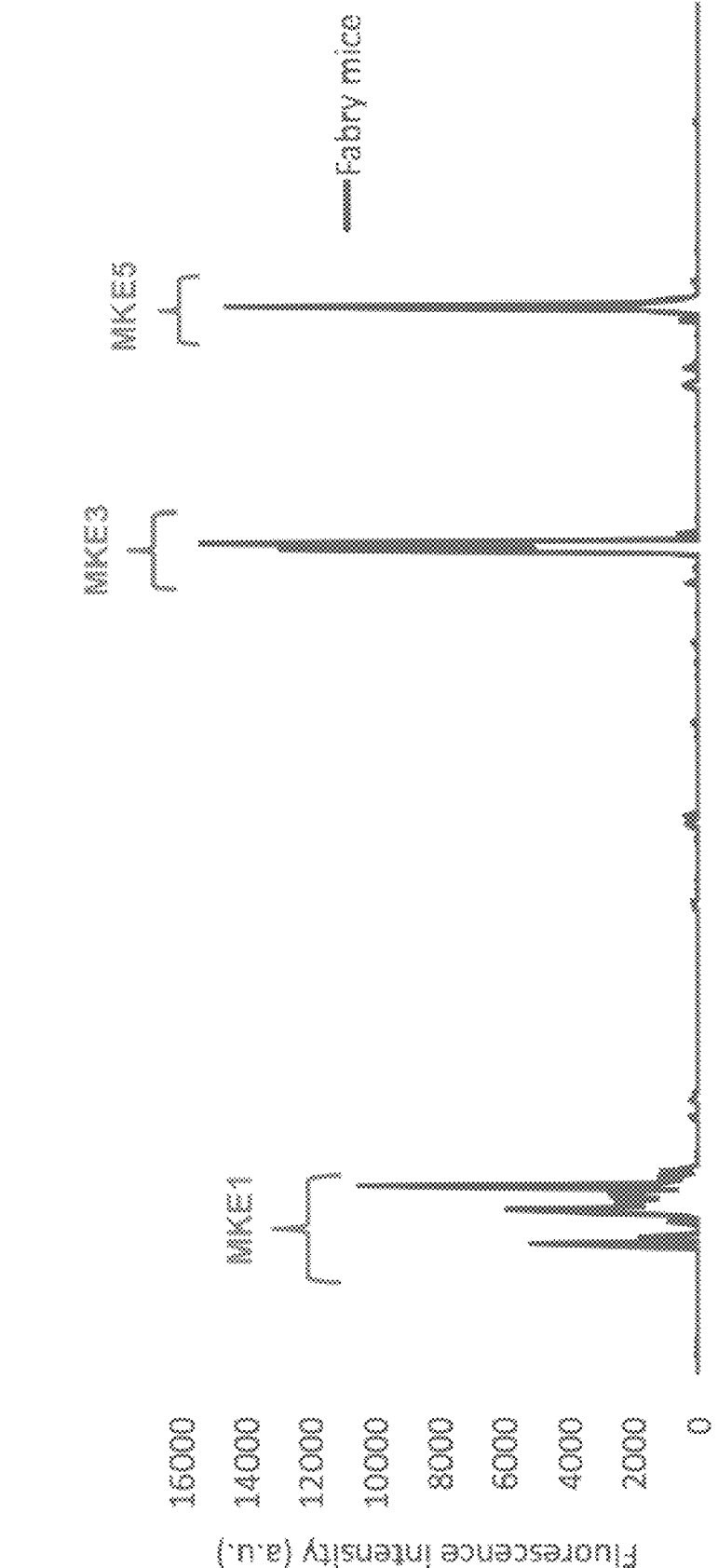
FIG. 4. An anti-α-gal A immune response generated in Fabry mice was evaluated by ELISA. PEPperMAP confirmed that the epitope profile detected was similar to that of the high-titer patients (3 of the 5 identified epitopes were present).
Figure 5:
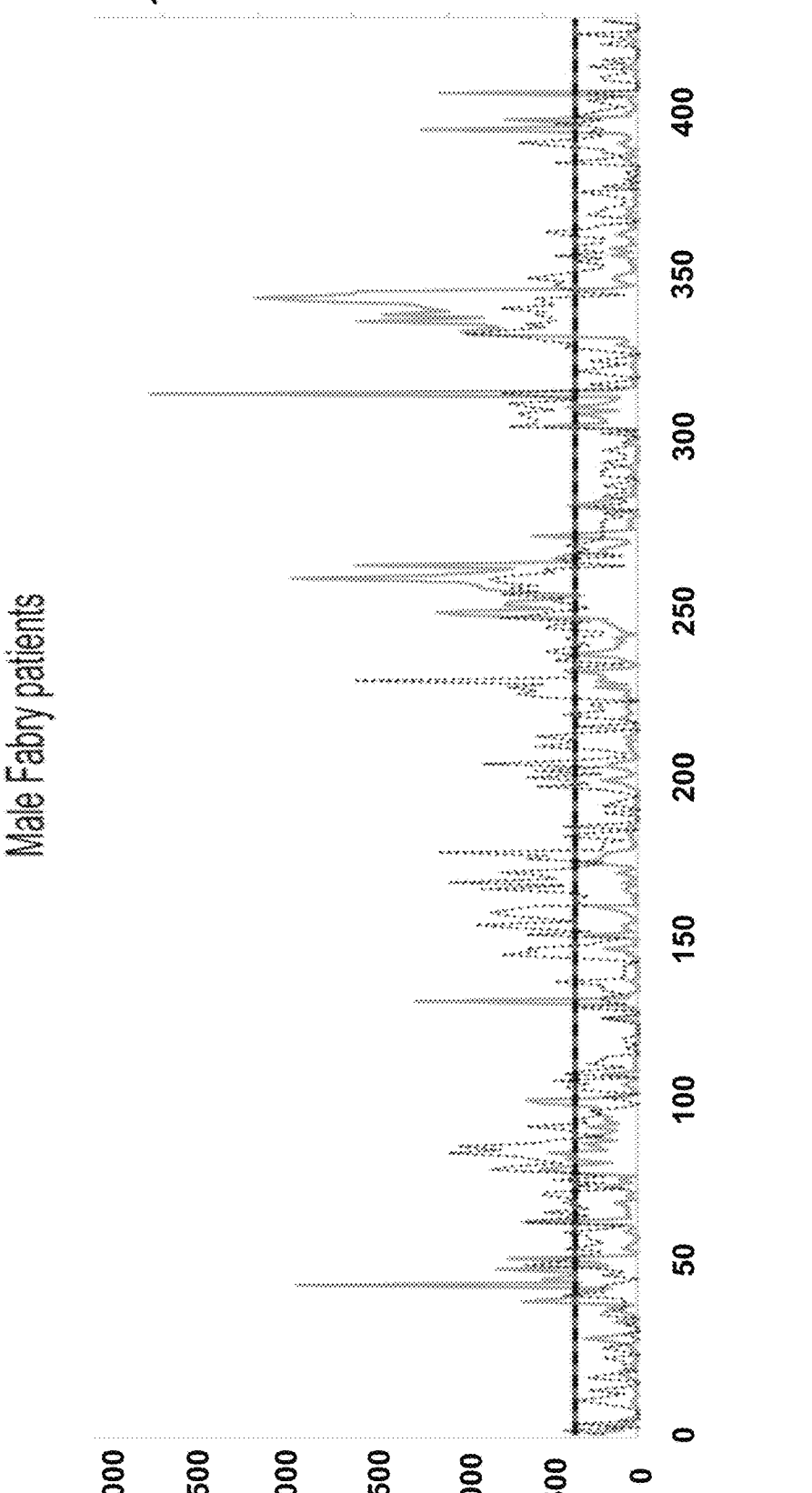
FIG. 5. IgG epitope mapping revealed many sites within the α-gal A protein that were immunogenic. Several sites were identified as being immunogenic across male Fabry patients, female Fabry patients, and Fabry mice.
Figure 5:
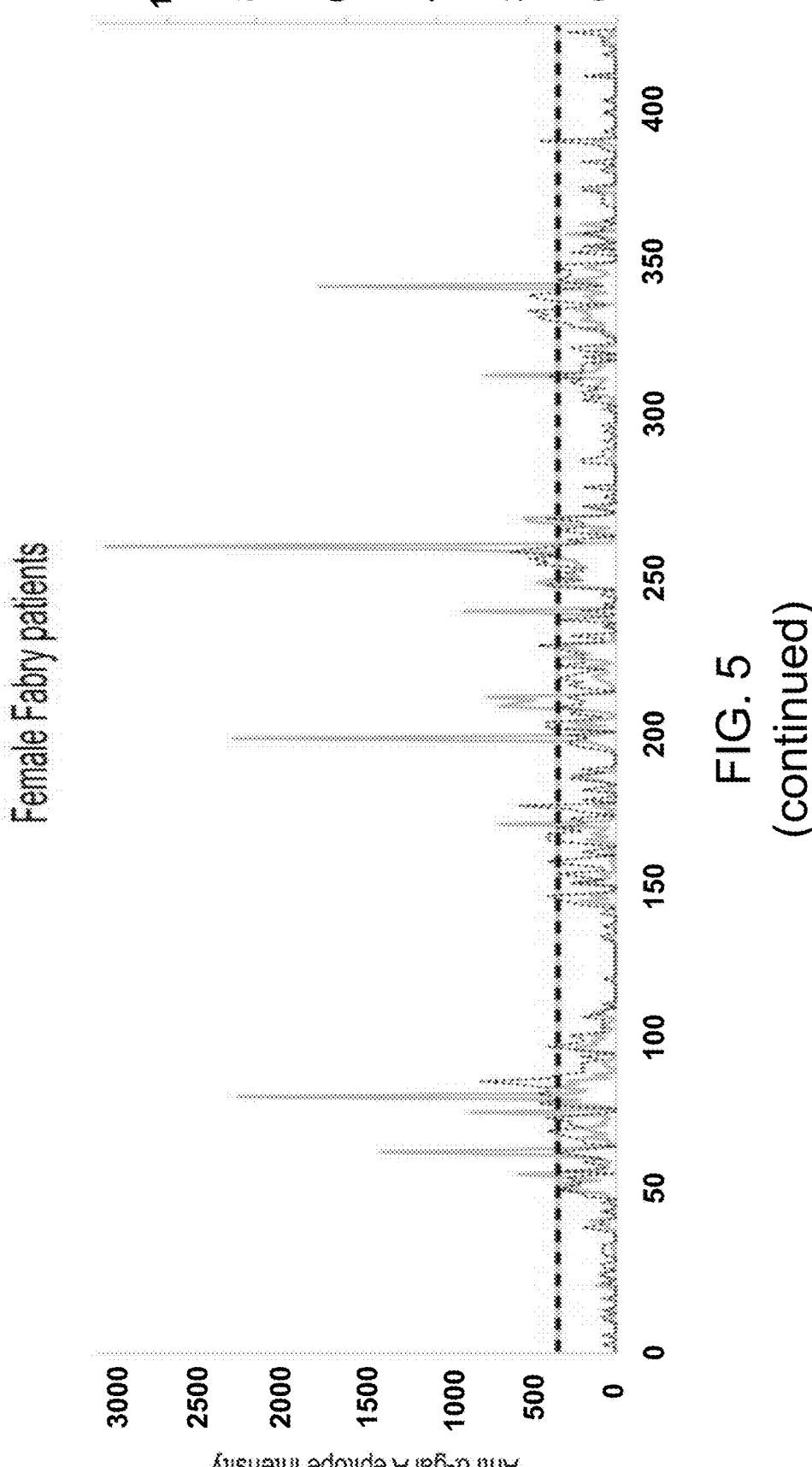
Figure 5:
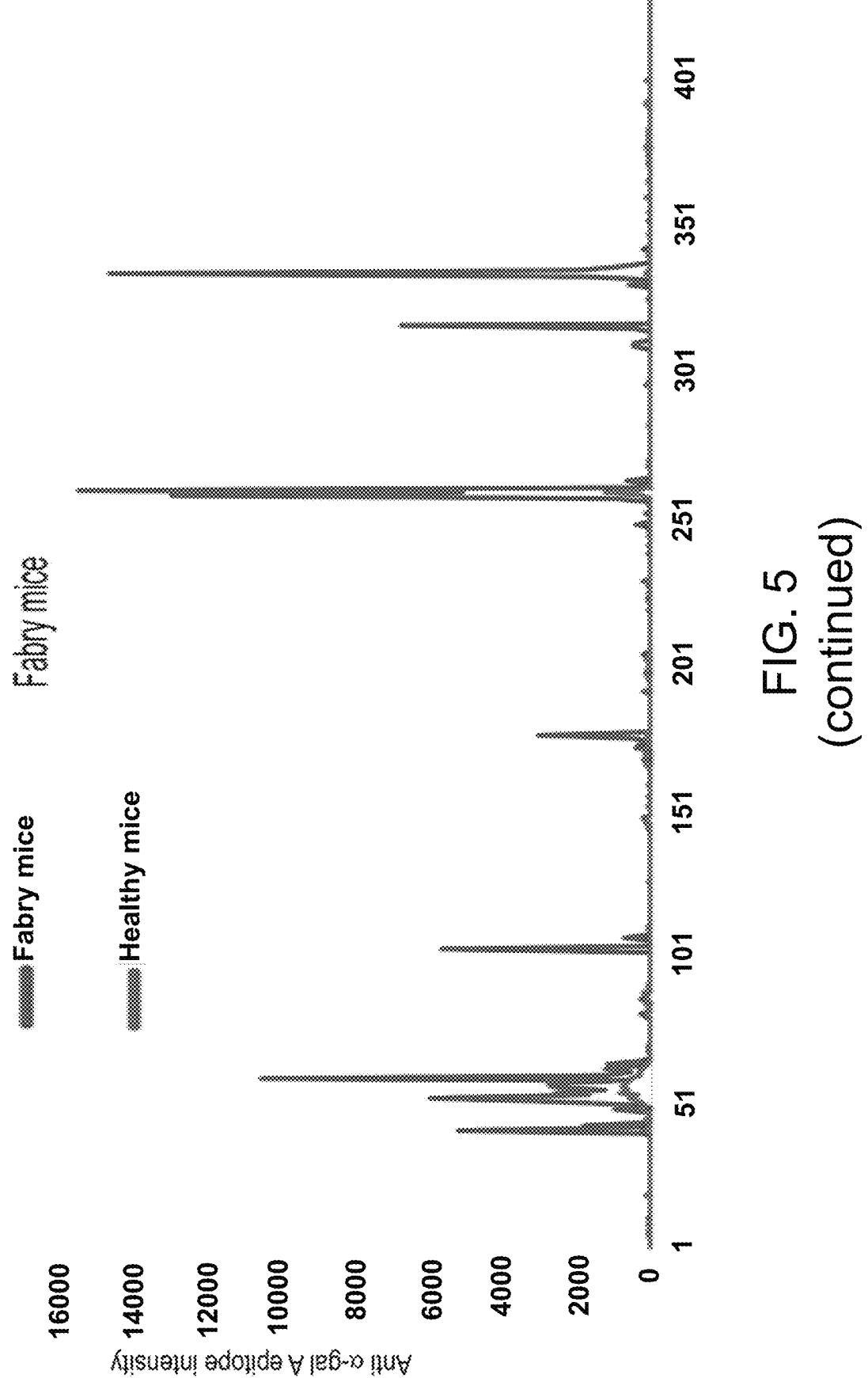

The same analyses were performed in α-gal A immunized Fabry mice to test if mice have an analogous immune reaction. FIG. 4 shows the PEPperMAP which confirmed that the epitope profile detected in mice was similar to that of the high-titer patients (3 of the 5 identified epitopes were present). A comparison of the human and mouse data is shown in FIG. 5. Table 1 lists the immunoreactive α-gal A epitopes identified in male and female Fabry patients as well as Fabry mice. Epitopes that were characterized as strongly immunoreactive are highlighted in bold.

TABLE 1

List of anti-α-gal A immunoreactive epitopes.

| | Epitope | Position | Males Response* | Females Response* | Mouse Response |
|---|---|---|---|---|---|
| A | LHWERF (SEQ ID NO: 2) | 45-50 | 3.18 | — | YES |
| B | DCQEEPDSCI (SEQ ID NO: 3) | 55-64 | 6.34 | — | YES |
| C | FMEMAELMVSEQ (SEQ ID NO: 4) | 69-79 | 1.69 | 1.79 | no |
| D | KDAGYEY (SEQ ID NO: 5) | 82-88 | 5.32 | 21.18 | no |
| E | DDCWMA (SEQ ID NO: 6) | 92-97 | 2.91 | 2.2 | no |
| F | EGRLQADPQRF (SEQ ID NO: 7) | 103-113 | 1.76 | — | no |
| G | TCAGF (SEQ ID NO: 8) | 141-145 | 1.84 | — | no |
| H | DIDAQTF (SEQ ID NO: 9) | 153-159 | 2.81 | 2.31 | no |
| I | DLLKFDGC (SEQ ID NO: 10) | 165-172 | 1.09 | 6.49 | YES |
| J | ENLAD (SEQ ID NO: 11) | 178-182 | 2.08 | 1.23 | no |
| K | IVYSCEW (SEQ ID NO: 12) | 198-204 | 2.03 | 21.5 | no |
| L | PLYMWPFQ (SEQ ID NO: 13) | 205-212 | 0.73 | — | no |
| M | YCNHW (SEQ ID NO: 14) | 222-226 | 2.31 | 3.41 | no |
| N | SWKSI (SEQ ID NO: 15) | 235-239 | 3.86 | - | no |
| O | LDWTSFNQER (SEQ ID NO: 16) | 243-252 | 11.07 | 3.75 | no |
| P | IVDVA (SEQ ID NO: 17) | 253-257 | 19.18 | 8.81 | YES |
| Q | NDPDML (SEQ ID NO: 18) | 263-268 | 15.56 | 28.61 | no |
| R | ALLQD (SEQ ID NO: 19) | 309-313 | 56.96 | 7.26 | no |

TABLE 1-continued

List of anti-α-gal A immunoreactive epitopes.

| | Epitope | Posi- tion | Males Re- sponse* | Females Re- sponse* | Mouse Re- sponse |
|---|---|---|---|---|---|
| S | QLRQGDNF (SEQ ID NO: 20) | 330-337 | 9.77 | 2.15 | YES |
| T | EVWERPLSG (SEQ ID NO: 21) | 338-346 | 20.33 | 16.62 | no |
| U | WAVAMIN (SEQ ID NO: 22) | 349-355 | 1.73 | 1.77 | no |
| V | EIGGPRSY (SEQ ID NO: 23) | 358-365 | 1.48 | 6.77 | no |

*Intensity per epitope/global mean in arbitrary units.

Example 2: Modification of α-gal A to Reduce Immunogenicity

Novel α-gal A variants were selected using for further testing using in silico analyses. Specifically, the selected mutations were predicted to maintain enzyme functionality (software used: PolyPhen-2) while reducing immunogenicity (databases used: CTLpred, Immunomedicine group, MHCBP, IEDB.org, SVRMHC, BcePred, SVMTrip, PRE-DIVAC, EpiJen). Importantly, amino acid mutations that are known to be associated with Fabry disease were excluded from the list of candidate mutations (databases used: HGMD, Fabrydatabase, Fabry_CEP). The 35 selected α-gal A mutations are shown in Table 2 and in FIG. 6. Notably, these mutations are found in three of the five reactive epitopes identified in Example 1.

TABLE 2

List of mutations that do not affect the functionality of the protein and make it less immunogenic (according the prediction software).

| 58/72 | E58N E66P M70H | E59N M70A M70Q | D61N M70R M70I | S62R M70N M70L | S62N M70D M70K | S62T M70G M70P |
|---|---|---|---|---|---|---|
| 74-101 | S78D E79G D101N | S78E D83E D101E | S78V A84I | E79A A84V | E79N Y86L | E79D R100F |
| 309-323 | A309N | A318G | P323R | | | |

Example 3: In Vitro Testing of Selected α-gal A Variants

Figure 7A:
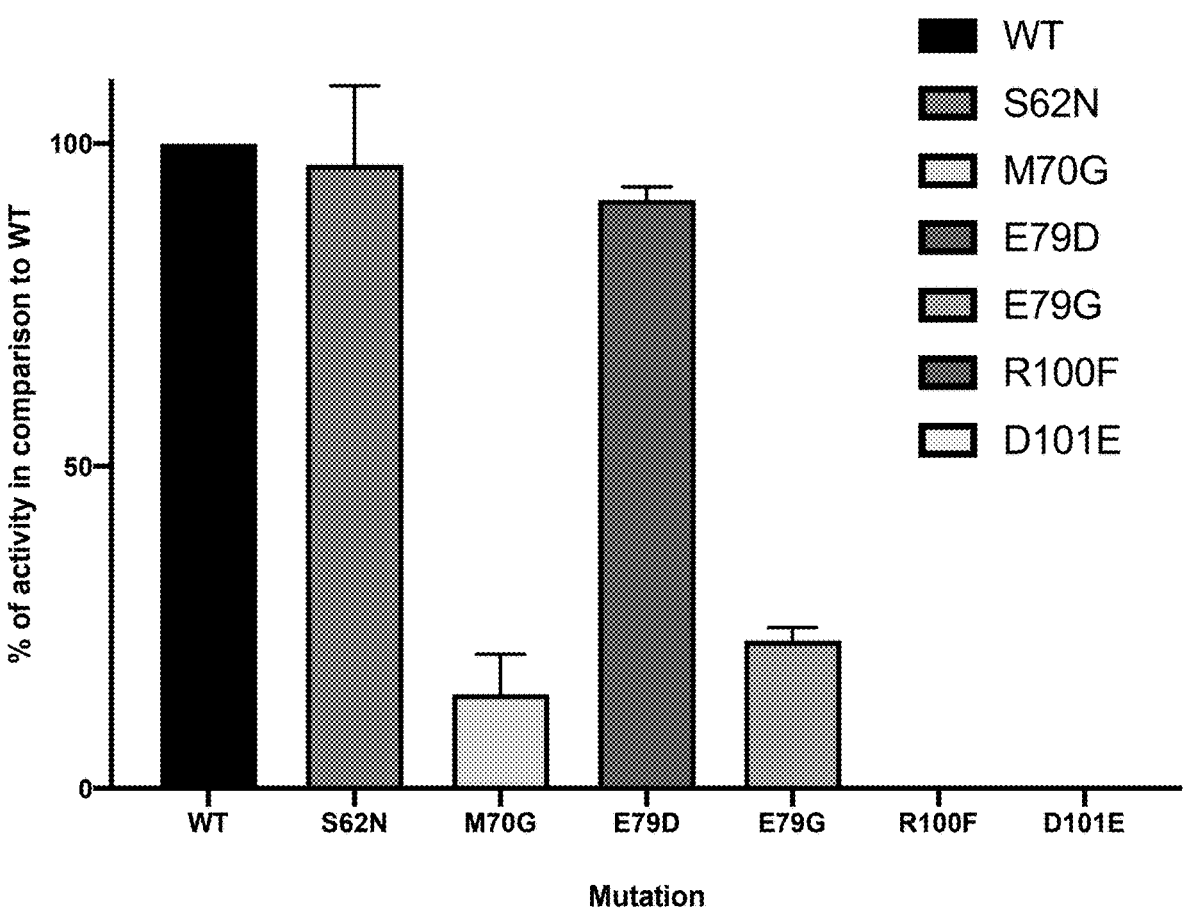
FIG. 7A. Enzyme activity assays were performed on media collected from cultured cells expressing the six indicated α-gal A variants. Enzyme activity is expressed as a percentage of wild-type activity. Three of the 7 mutant secreted proteins retained near wild-type enzymatic activity.
Figure 7B:
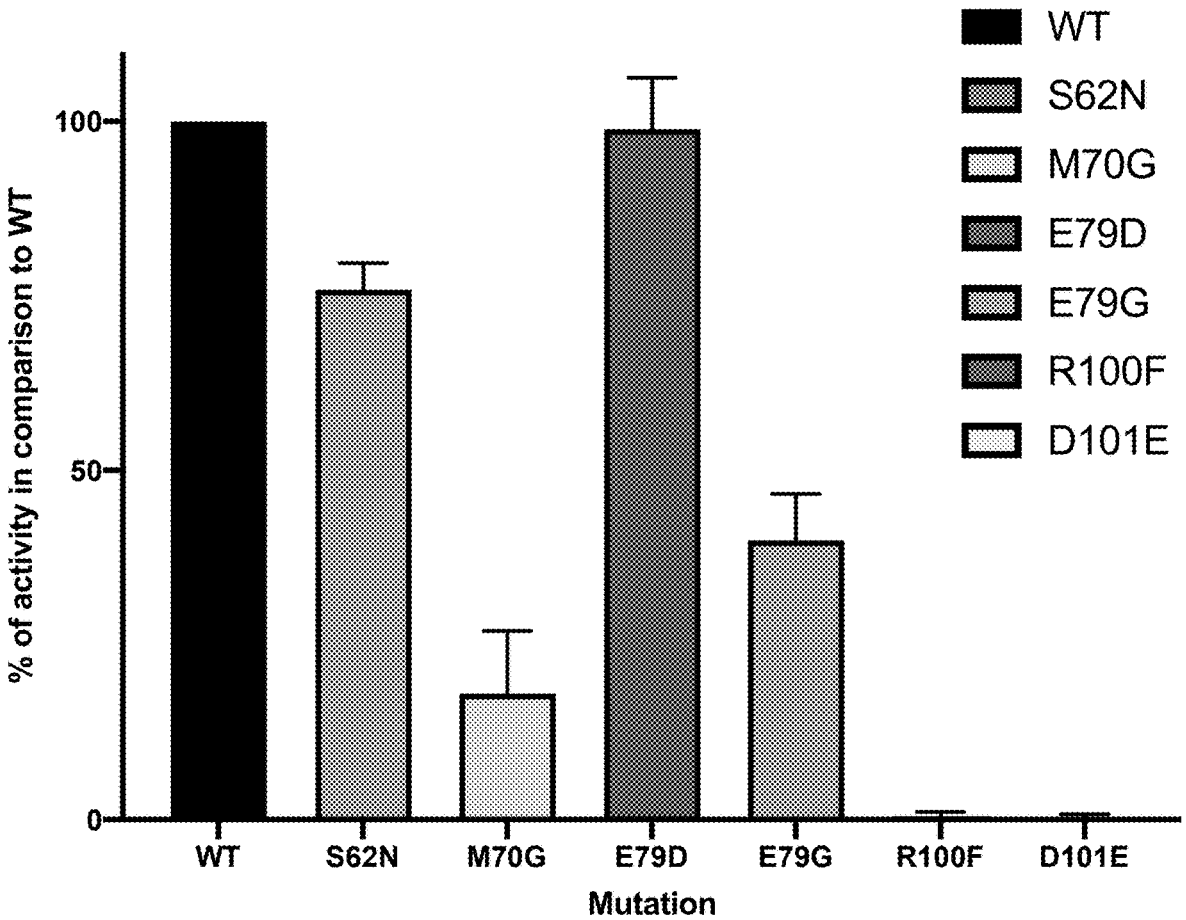
FIG. 7B. Enzyme activity assays were performed on the lysate of cells expressing the six indicated α-gal A variants. Enzyme activity is expressed as a percentage of wild-type activity. Intracelluar enzyme activity retention was similar to that of secreted in FIG. 7A.
Figure 8:
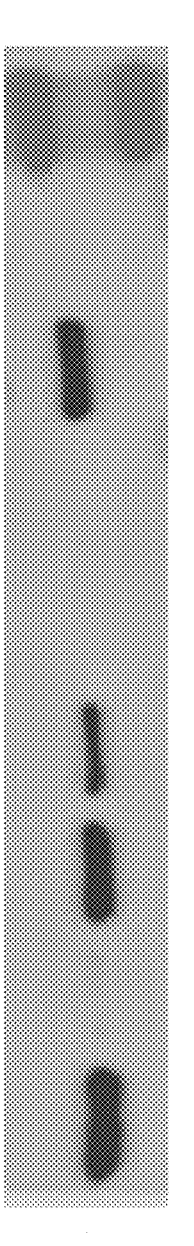
FIG. 8. Protein expression of the α-gal A variants was confirmed using western blot analysis with an anti-α-gal A antibody. Expression correlated with the level of enzyme activity in FIGS. 7A and 7B.
Figure 8:
Figure 8:
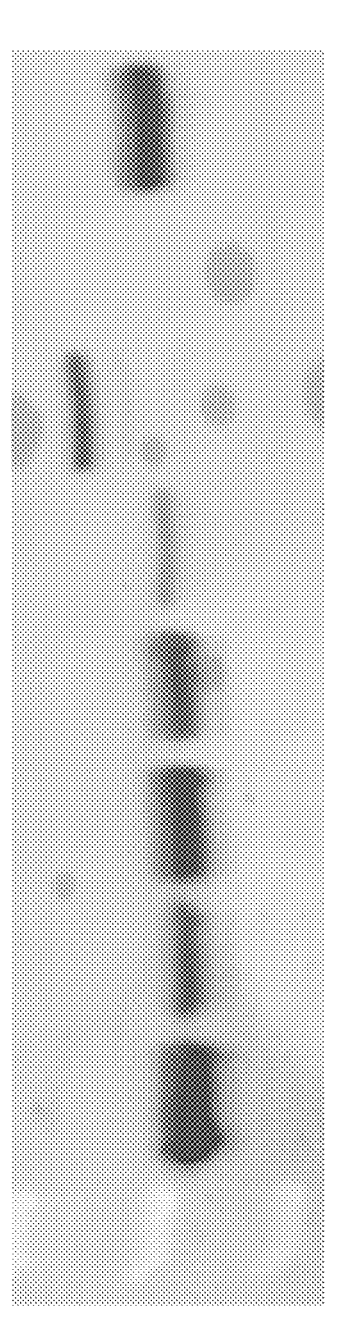
Figure 8:
Figure 9:
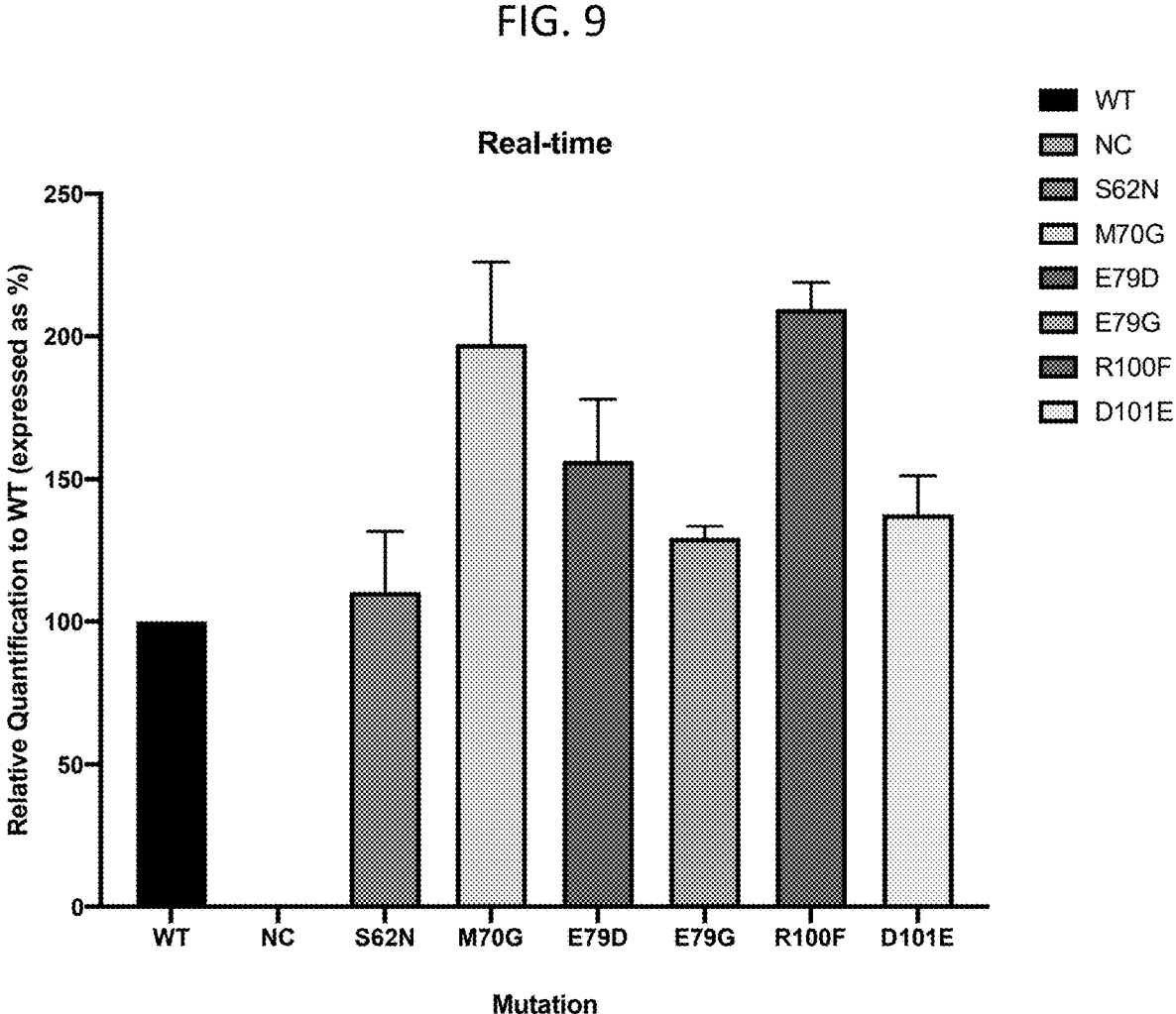
FIG. 9. mRNA expression of the α-gal A variants was confirmed using quantitative reverse transcription PCR. The results are shown as a percentage of wild-type expression. Transcript for each of the variant proteins was either equal to or above the level of transcript for the wild-type α-gal A.

Six mutations (S62N, M70G, E79D, E79G, R100F, and D101E) were selected for a preliminary in vitro analysis. The mutations were generated using site-directed mutagenesis into pcDNA3.4 containing the coding sequence for amino acids 1-429 of human α-gal A, verified by sequencing, and transfected by standard Lipofectamine techniques into HEK 293T cells for expression in triplicate. Enzyme activity assays were performed using both the cell culture media (FIG. 7A) and the lysate of the transfected cells (FIG. 7B). Activity was determined by a fluorometric assay which measured the conversion of 4-methylumbelliferyl-α-D-galactopyranoside substrate. Expression of the mutant proteins was confirmed using western blot analysis in the presence of WPRE (FIG. 8) and quantitative reverse transcription PCR (FIG. 9). The results of these studies demonstrate that two of tested variants (S62N and E79D) were expressed well at the protein level and exhibited enzyme activity levels that were comparable to the wild-type enzyme.

The remaining candidate mutations (listed in Table 2) will be analyzed in future studies. The immunogenicity of any promising α-gal A variants will then be evaluated in vivo using a Fabry mouse model.

Each publication, patent, and patent publication cited in this disclosure is incorporated in reference herein in its entirety. The present invention is not intended to be limited to the foregoing examples but encompasses all such modifications and variations as come within the scope of the appended claims.

What is claimed is:

1. A virus comprising an expression construct comprising a nucleic acid sequence encoding a mutant α-galactosidase A protein (α-gal), wherein the mutant α-gal comprises a S62N amino acid change, wherein the amino acid change is relative to SEQ ID NO: 1, wherein the mutant a-gal has at least 98% identity to SEQ ID NO: 1, and wherein the virus is a retrovirus, adenovirus, or adeno-associated virus.

2. A host cell comprising the virus of claim 1.

3. The virus of claim 1, wherein the mutant α-gal consists of a S62N amino acid change, relative to SEQ ID NO: 1.

4. The host cell of claim 2, wherein the cell is a CD34+ stem cell or a T cell.

5. The virus of claim 1, wherein the mutant α-gal further comprises one or more amino acid change selected from the group consisting of E58N, E59N, D61N, E66P, M70A, M70R, M70N, M70D, M70G, M70H, M70Q, M70I, M70L, M70K, M70P, S78D, S78E, S78V, E79A, E79N, E79D, E79G, D83E, A84I, A84V, Y86L, R100F, D101N, D101E, A309N, A318G, and P323R.

*     *     *     *     *

SEQUENCE LISTING

<160> NUMBER OF SEQ ID NOS: 23

<210> SEQ ID NO 1
<211> LENGTH: 429
<212> TYPE: PRT
<213> ORGANISM: Homo sapiens

<400> SEQUENCE: 1

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
```

-continued

```
                85                    90                    95
Ala Pro Gln Arg Asp Ser Glu Gly Arg Leu Gln Ala Asp Pro Gln Arg
            100                   105                   110

Phe Pro His Gly Ile Arg Gln Leu Ala Asn Tyr Val His Ser Lys Gly
            115                   120                   125

Leu Lys Leu Gly Ile Tyr Ala Asp Val Gly Asn Lys Thr Cys Ala Gly
            130                   135                   140

Phe Pro Gly Ser Phe Gly Tyr Tyr Asp Ile Asp Ala Gln Thr Phe Ala
145                   150                   155                   160

Asp Trp Gly Val Asp Leu Leu Lys Phe Asp Gly Cys Tyr Cys Asp Ser
                165                   170                   175

Leu Glu Asn Leu Ala Asp Gly Tyr Lys His Met Ser Leu Ala Leu Asn
            180                   185                   190

Arg Thr Gly Arg Ser Ile Val Tyr Ser Cys Glu Trp Pro Leu Tyr Met
            195                   200                   205

Trp Pro Phe Gln Lys Pro Asn Tyr Thr Glu Ile Arg Gln Tyr Cys Asn
            210                   215                   220

His Trp Arg Asn Phe Ala Asp Ile Asp Asp Ser Trp Lys Ser Ile Lys
225                   230                   235                   240

Ser Ile Leu Asp Trp Thr Ser Phe Asn Gln Glu Arg Ile Val Asp Val
                245                   250                   255

Ala Gly Pro Gly Gly Trp Asn Asp Pro Asp Met Leu Val Ile Gly Asn
            260                   265                   270

Phe Gly Leu Ser Trp Asn Gln Gln Val Thr Gln Met Ala Leu Trp Ala
            275                   280                   285

Ile Met Ala Ala Pro Leu Phe Met Ser Asn Asp Leu Arg His Ile Ser
            290                   295                   300

Pro Gln Ala Lys Ala Leu Leu Gln Asp Lys Asp Val Ile Ala Ile Asn
305                   310                   315                   320

Gln Asp Pro Leu Gly Lys Gln Gly Tyr Gln Leu Arg Gln Gly Asp Asn
                325                   330                   335

Phe Glu Val Trp Glu Arg Pro Leu Ser Gly Leu Ala Trp Ala Val Ala
            340                   345                   350

Met Ile Asn Arg Gln Glu Ile Gly Gly Pro Arg Ser Tyr Thr Ile Ala
            355                   360                   365

Val Ala Ser Leu Gly Lys Gly Val Ala Cys Asn Pro Ala Cys Phe Ile
            370                   375                   380

Thr Gln Leu Leu Pro Val Lys Arg Lys Leu Gly Phe Tyr Glu Trp Thr
385                   390                   395                   400

Ser Arg Leu Arg Ser His Ile Asn Pro Thr Gly Thr Val Leu Leu Gln
                405                   410                   415

Leu Glu Asn Thr Met Gln Met Ser Leu Lys Asp Leu Leu
            420                   425
```

```
<210> SEQ ID NO 2
<211> LENGTH: 6
<212> TYPE: PRT
<213> ORGANISM: Homo sapiens

<400> SEQUENCE: 2

Leu His Trp Glu Arg Phe
1               5

<210> SEQ ID NO 3
<211> LENGTH: 10
```

```
<212> TYPE: PRT
<213> ORGANISM: Homo sapiens

<400> SEQUENCE: 3

Asp Cys Gln Glu Glu Pro Asp Ser Cys Ile
1               5                   10

<210> SEQ ID NO 4
<211> LENGTH: 12
<212> TYPE: PRT
<213> ORGANISM: Homo sapiens

<400> SEQUENCE: 4

Phe Met Glu Met Ala Glu Leu Met Val Ser Glu Gln
1               5                   10

<210> SEQ ID NO 5
<211> LENGTH: 7
<212> TYPE: PRT
<213> ORGANISM: Homo sapiens

<400> SEQUENCE: 5

Lys Asp Ala Gly Tyr Glu Tyr
1               5

<210> SEQ ID NO 6
<211> LENGTH: 6
<212> TYPE: PRT
<213> ORGANISM: Homo sapiens

<400> SEQUENCE: 6

Asp Asp Cys Trp Met Ala
1               5

<210> SEQ ID NO 7
<211> LENGTH: 11
<212> TYPE: PRT
<213> ORGANISM: Homo sapiens

<400> SEQUENCE: 7

Glu Gly Arg Leu Gln Ala Asp Pro Gln Arg Phe
1               5                   10

<210> SEQ ID NO 8
<211> LENGTH: 5
<212> TYPE: PRT
<213> ORGANISM: Homo sapiens

<400> SEQUENCE: 8

Thr Cys Ala Gly Phe
1               5

<210> SEQ ID NO 9
<211> LENGTH: 7
<212> TYPE: PRT
<213> ORGANISM: Homo sapiens

<400> SEQUENCE: 9

Asp Ile Asp Ala Gln Thr Phe
1               5

<210> SEQ ID NO 10
<211> LENGTH: 8
<212> TYPE: PRT
<213> ORGANISM: Homo sapiens
```

```
<400> SEQUENCE: 10

Asp Leu Leu Lys Phe Asp Gly Cys
1               5

<210> SEQ ID NO 11
<211> LENGTH: 5
<212> TYPE: PRT
<213> ORGANISM: Homo sapiens

<400> SEQUENCE: 11

Glu Asn Leu Ala Asp
1               5

<210> SEQ ID NO 12
<211> LENGTH: 7
<212> TYPE: PRT
<213> ORGANISM: Homo sapiens

<400> SEQUENCE: 12

Ile Val Tyr Ser Cys Glu Trp
1               5

<210> SEQ ID NO 13
<211> LENGTH: 8
<212> TYPE: PRT
<213> ORGANISM: Homo sapiens

<400> SEQUENCE: 13

Pro Leu Tyr Met Trp Pro Phe Gln
1               5

<210> SEQ ID NO 14
<211> LENGTH: 5
<212> TYPE: PRT
<213> ORGANISM: Homo sapiens

<400> SEQUENCE: 14

Tyr Cys Asn His Trp
1               5

<210> SEQ ID NO 15
<211> LENGTH: 5
<212> TYPE: PRT
<213> ORGANISM: Homo sapiens

<400> SEQUENCE: 15

Ser Trp Lys Ser Ile
1               5

<210> SEQ ID NO 16
<211> LENGTH: 10
<212> TYPE: PRT
<213> ORGANISM: Homo sapiens

<400> SEQUENCE: 16

Leu Asp Trp Thr Ser Phe Asn Gln Glu Arg
1               5                   10

<210> SEQ ID NO 17
<211> LENGTH: 5
<212> TYPE: PRT
<213> ORGANISM: Homo sapiens

<400> SEQUENCE: 17
```

-continued

Ile Val Asp Val Ala
1               5

<210> SEQ ID NO 18
<211> LENGTH: 6
<212> TYPE: PRT
<213> ORGANISM: Homo sapiens

<400> SEQUENCE: 18

Asn Asp Pro Asp Met Leu
1               5

<210> SEQ ID NO 19
<211> LENGTH: 5
<212> TYPE: PRT
<213> ORGANISM: Homo sapiens

<400> SEQUENCE: 19

Ala Leu Leu Gln Asp
1               5

<210> SEQ ID NO 20
<211> LENGTH: 8
<212> TYPE: PRT
<213> ORGANISM: Homo sapiens

<400> SEQUENCE: 20

Gln Leu Arg Gln Gly Asp Asn Phe
1               5

<210> SEQ ID NO 21
<211> LENGTH: 9
<212> TYPE: PRT
<213> ORGANISM: Homo sapiens

<400> SEQUENCE: 21

Glu Val Trp Glu Arg Pro Leu Ser Gly
1               5

<210> SEQ ID NO 22
<211> LENGTH: 7
<212> TYPE: PRT
<213> ORGANISM: Homo sapiens

<400> SEQUENCE: 22

Trp Ala Val Ala Met Ile Asn
1               5

<210> SEQ ID NO 23
<211> LENGTH: 8
<212> TYPE: PRT
<213> ORGANISM: Homo sapiens

<400> SEQUENCE: 23

Glu Ile Gly Gly Pro Arg Ser Tyr
1               5